United States Patent
Lambrecht

(10) Patent No.: US 6,897,313 B2
(45) Date of Patent: May 24, 2005

(54) PRODUCTION OF 2-ETHYL-3-METHYL-1,4 DIAZINE

(75) Inventor: Stefan Lambrecht, Holzminden (DE)

(73) Assignee: Symrise GmbH & Co. KG (DE)

( * ) Notice: Subject to any disclaimer, the term of this patent is extended or adjusted under 35 U.S.C. 154(b) by 160 days.

(21) Appl. No.: 10/275,539

(22) PCT Filed: Apr. 26, 2001

(86) PCT No.: PCT/EP01/04697

§ 371 (c)(1),
(2), (4) Date: Nov. 6, 2002

(87) PCT Pub. No.: WO01/85703

PCT Pub. Date: Nov. 15, 2001

(65) Prior Publication Data

US 2003/0134022 A1 Jul. 17, 2003

(30) Foreign Application Priority Data

May 8, 2000 (DE) ......................... 100 22 361

(51) Int. Cl.$^7$ .............................................. C07D 24/12
(52) U.S. Cl. ..................................................... 544/410
(58) Field of Search ......................................... 344/410

(56) References Cited

PUBLICATIONS

Helvetica Chimica Acta, 50, (month unavailable) 1967, pp. 1754–1758, "Pyrazines", I. Synthese de méthyl–2–pyrazines alcoylées en 3, par condensation de l' éthylènediamine avac les dioxo–2,3–alcanes, par I. Flament et M. Stoll.

Nakatani Y. et al.: "Synthèse facile de pyrazines disubstituées en 2 et 3" Agricultural and Biological Chemistry., Bd. 37, Nr. 6, 1973, Seiten 1509–1510, XP001024034 Japan Soc. For Bioscience, Biotechnology and Agrochem. Tokyo., JP ISSN: 0002–1369 in der Anmeldung erwähnt das ganze Dokument.

Chemical Abstracts, vol. 104, No. 19, May 12, 1986 Columbus, Ohio, US; abstract no. 168437, Tsai, Songchuan et al: "Syntheses of pyrazines. I" XP002176855 in der Anmeldung erwähnt Zusammenfassung & Nanjing Daxue Xuebao, Ziran Dexue (1984), (2), 245–9, 2 Plates.

Chemical Abstracts, vol. 52, No. 14, .Jul. 25, 1958 Columbus, Ohio, US; abstract no. 111862a, XP002176857 Zusammenfassung & Takeo Ishigure: "Syntheses of piperazines. VIII" Yakugaku Zasshi Bd. 78, 1958, Seiten 229–231.

Rizzi G. P.: "Some reactions of methylpyrazines with organolithium reagents" Journal of Organic Chemistry., Bd. 33, Nr, Apr. 4, 1988, Seiten 1333–1337, XP002176853 American Chemical Society. Easton., US ISSN: 0022–3263 Seite 1336. Hersteilung der Verbindungen 14 und 15 und Referenz 15.

Chemical Abstracts, vol. 88, No. 15, Apr. 10, 1978 Columbus, Ohio, US; abstract no. 105412, Enomoto, Yoshiyuki et al; Pyrazine derivatives XP002176857 in der Anmeldung erwähnt Zusammenfassung & JP 52 136182 A (Ogawa and Co., Ltd., Japan) Nov. 14, 1977

*Primary Examiner*—Richard L. Raymond
*Assistant Examiner*—Hong Liu
(74) *Attorney, Agent, or Firm*—Pendorf & Cutliff

(57) ABSTRACT

The invention relates to a novel, industrial synthesis of 2-ethyl-3-methyl-1,4-diazine.

13 Claims, No Drawings

PRODUCTION OF 2-ETHYL-3-METHYL-1,4 DIAZINE

The invention relates to a novel industrial synthesis of 2-ethyl-3-methyl-1,4-diazine in which solvents which are problematic for the environment and safety can be omitted, only a few process steps are required and the use of processing aids, for example solvents, in this process is minimal.

2-Ethyl-3-methyl-1,4-diazine is an important fragrance material (Allured's Flavor and Fragrance Materials—1995, Allured Publishing Corporation, 1995, p. 127). An industrial process which produces 2-ethyl-3-methyl-1,4-diazine in a simple and inexpensive manner is therefore of great economic interest.

The production of 2-ethyl-3-methyl-1,4-diazine is known per se. It is produced starting from 2,3-pentanedione and 1,2-ethanediamine in a two-stage process which is illustrated by the following reaction scheme:

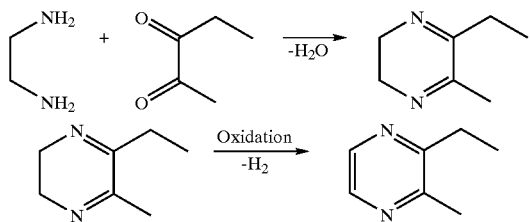

However, the known methods of synthesis are unsuitable for an industrial reaction. In particular, the following criteria must be met for an industrial synthesis:

use of solvents which are unproblematic from safety and environmental aspects
few process steps
a high space-time yield
hazard-free procedure The known syntheses do not meet these conditions. For example, environmentally critical oxidizing agents such as copper chromite (*Helv. Chim. Acta* 1967, 50, 1754) are used. Handling environmentally critical substances requires a complex reaction procedure and safe deposition of the residues. Hazardous materials such as ethylene glycol (*Agr. Biol. Chem.* 1973, 37, 1509) are used as solvents. Thus, in the case of ethylene glycol, the maximum air concentration in the workplace is 10 ppm (MAC-und BAT-Werte-Liste [List of MAC and BAT values], 1999, Wiley-VCH, Weinheim). The number of individual process steps is high (*Nanjing Daxue Xuebo, Ziran Kexue* 1984, 245 and above authors). The process of JP 52 136 182 also produces 2-ethyl-3-methyl-1,4-diazine in the presence of ecologically harmful oxidizing agents such as manganese oxide, copper oxide or lead oxide. In addition, a large amount of these oxidizing agents is used, which makes production difficult and the procedure expensive.

An industrial process which produces 2-ethyl-3-methyl-1,4-diazine in a simple and inexpensive manner is therefore of great economic interest.

A process for producing 2-ethyl-3-methyl-1,4-diazine has been found characterized in that 2,3-pentanedione and 1,2-ethanediamine are reacted in, as solvent, an aliphatic monoalcohol, diol or triol containing three to eight carbon atoms with addition of catalytic amounts of an alkaline substance and are then added dropwise to a solution of an alkaline compound in an aliphatic monoalcohol, diol or triol having three to eight carbon atoms and a catalyst with dehydrogenating activity, which can be applied to a support, and the product is separated off by steam distillation.

By means of the present invention it is possible to overcome said disadvantages and to provide an industrially expedient process.

Aliphatic monoalcohols, diols or triols are, for example, butanol, pentanol, hexanol, heptanol, octanol, 1,2-butanediol, 1,4-butanediol, 1,3-propanediol, 1,2-propanediol and glycerol.

Preferred aliphatic monoalcohols, diols or triols are 1,3-propanediol, 1,2-propanediol and glycerol.

Particular preference is given to 1,2-propanediol.

The alkaline substance can be, for example, an alkali metal carbonate, an alkali metal hydrogencarbonate or an alkali metal acetate.

Preferred alkaline substances are alkali metal carbonates.

A particularly preferred alkaline substance is potassium carbonate.

Catalysts with dehydrogenating activity in the inventive meaning contain elements of subgroup 1, 2, 6, 7 or 8, their compounds, oxides, alloys or mixtures. These catalysts can be used, for example, in finely divided form, applied to supports, or together with other metals or other metal compounds. The catalysts with dehydrogenating activity can be doped with one or more metals as desired or their compounds.

Suitable catalysts with dehydrogenating activity can contain, for example, copper, silver, zinc, chromium, molybdenum, tungsten, manganese, rhenium, iron, ruthenium, osmium, cobalt, rhodium, iridium, nickel, palladium or platinum.

Particularly advantageous catalysts with dehydrogenating activity are those containing the elements palladium, platinum, ruthenium or rhodium.

A very particularly preferred catalyst with dehydrogenating activity is palladium, which can be applied to a support material.

The inventive catalysts with dehydrogenating activity can be applied to organic or inorganic support materials. Advantageous support materials which may be mentioned are activated carbon, carbon, aluminum oxides, metal oxides, silica gels, zeolites, clays, clay granules, amorphous aluminum silicates, or other inorganic or polymeric supports. A preferred support material is activated carbon.

For the inventive process, in general, catalysts with dehydrogenating activity are used on a support material, with the percentage by weight of the element of subgroup 1, 2, 6, 7 or 8 being 1 to 15% by weight, preferably 5 to 10% by weight, of the catalyst weight.

Alkaline compounds can be, for example, alkali metal alkoxides, alkali metal hydroxides or alkaline earth metal hydroxides. Preference is given to potassium hydroxide, sodium hydroxide, potassium methoxide, potassium ethoxide, sodium methoxide and sodium ethoxide.

The inventive process is advantageous compared with the known processes. It can employ problem-free solvents, for example 1,2-propanediol which is permitted for use in foods. It is surprising here that the amount of solvent in the first process step can be very low without reducing yield. As a result the space-time yield is increased and the economic efficiency of the process is thereby improved. It is also surprising that the solvent after the reaction to give the intermediate need not be removed. The reaction mixture can be used in the second reaction directly and without further purification or isolation operations. The use of an inventive solvent, for example 1,2-propanediol, also makes possible simple and economic isolation of the product, since 2-ethyl- 3-methyl-1,4-diazine can be separated from the reaction mixture in a steam distillation. Other alcohols such as ethanol (*Agr. Biol. Chem.* 1973, 37, 1509) have boiling points which are too low, so that steam distillation is impossible. Other higher alcohols have insufficient solubility properties, so that their use is also not advantageous.

It is in addition surprising that even the addition of catalytic amounts of the inventive alkaline substances is sufficient to stabilize the resultant intermediate. This is particularly advantageous, since small amounts of the inventive alkaline substances remain in solution and thus handling is greatly simplified.

It is further surprising that the reaction mixture from the first process step can advantageously be added dropwise to a solution of the inventive alkaline compounds in an inventive aliphatic diol or triol having three to eight carbon atoms and an inventive catalyst with dehydrogenating activity on a support. Since, in the reaction, gas is formed, in this manner the spontaneous release of a large amount of gas is avoided. This greatly increases the safety of the process.

The first step of the inventive process is generally carried out in the temperature range from −10 to 100° C., preferably at 10 to 60° C. The feed materials 2,3-pentanedione and 1,2-ethanediamine can be added in the same molar amounts or in deficit or excess. Preference is given to a molar ratio of 2,3-pentanedione to 1,2-ethanediamine of from 0.1 to 1 to 2 to 1. The amount of the inventive alkaline substance can be 0.0001 to 40% by weight, preferably 0.001 to 5% by weight, based on 2,3-pentanedione.

The solvent used is an aliphatic diol or triol having three to eight carbon atoms, preferably 1,2-propanediol. The amount of solvent can be between 10 and 300% by weight, based on 2,3-pentanedione.

The second step of the inventive process is generally carried out in the temperature range of 70 to 180° C., preferably 80 to 130° C. The reaction mixture of the first stage is added dropwise at this temperature to a solution of an inventive alkaline compound in an inventive diol or triol having three to eight carbon atoms and a catalyst with dehydrogenating activity. The amount of catalyst can be 0.0001 to 1% by weight, preferably 0.001 to 0.1% by weight, based on 2,3-pentanedione used. The amount of the alkaline compound can be between 0.2 and 3 molar equivalents, preferably between 0.4 and 1.5 molar equivalents, based on 2,3-pentandione.

The process can be carried out at atmospheric pressure and at superatmospheric pressure or reduced pressure. For example, the following pressure range may be mentioned: 0.1 to 10 bar, preferably 0.2 to 5 bar.

The 2-ethyl-3-methyl-1,4-diazine is separated off from the reaction mixture according to the inventive process by steam distillation at atmospheric pressure or in vacuo, preferably in vacuo, particularly preferably at a vacuum of 10 to 500 mbar.

EXAMPLE 1

Preparation of 2-ethyl-3-methyl-1,4-diazine Using Potassium Hydroxide as Alkaline Compound First Process Step 100 ml of 1,2-propanediol and 0.5 g of potassium carbonate were charged and cooled to 0° C. At this temperature, 247 g of 2,3-pentanedione and 158 g of 1,2-ethanediamine were added dropwise (reaction mixture first stage).

Second Process Step 200 ml of 1,2-propanediol, 90 g of potassium hydroxide and 0.8 g of palladium on activated carbon, 5% by weight of the catalyst weight, were mixed and heated to 100° C. At this temperature the reaction mixture first stage was added dropwise. The further reaction time was 3 hours.

The product was separated off from the reaction mixture by steam distillation at 125 mbar. The distillate was saturated with sodium chloride and extracted with methyl tert-butyl ether.

2-Ethyl-3-methyl-1,4-diazine was obtained in a yield of 56%.

Boiling point: 61° C. (15 mbar).

EXAMPLE 2

Production of 2-ethyl-3-methyl-1,4-diazine Using Sodium Methoxide as Alkaline Compound First Process Step 42 g of 1,2-propanediol and 0.21 g of potassium carbonate were charged and 113 g of 2,3-pentanedione and 65.5 g of 1,2-ethanediamine were added dropwise at 20° C. (reaction mixture first stage).

Second Process Step 184 g of 1,2-propanediol, 100 g of sodium methoxide and 0.32 g of palladium on activated carbon, 5% by weight of the catalyst weight, were mixed and heated to 100° C. At this temperature the reaction mixture first stage was added dropwise. The further reaction time was 3 hours.

The product was separated off from the reaction mixture by steam distillation at 130 mbar. The distillate was saturated with sodium chloride and extracted with methyl tert-butyl ether.

2-Ethyl-3-methyl-1,4-diazine was obtained in a yield of 60%.

Boiling point: 61° C. (15 mbar).

EXAMPLE 3

Production of 2-ethyl-3-methyl-1,4-diazine in the Presence of Various Catalysts with Dehydrogenating Activity (see Table 1)

First Process Step 41 g of 1,2-propanediol and 0.21 g of potassium carbonate were charged at 20° C. At this temperature, 100 g of 2,3-pentanedione and 65.2 g of 1,2-ethanediamine were added dropwise (reaction mixture first stage).

Second Process Step 82 g of 1,2-propanediol, 36.7 g of potassium hydroxide and the corresponding amount of the catalyst with dehydrogenating activity (see Table 1) were mixed and heated to the specified temperature. At this temperature the reaction mixture first stage was added dropwise. The further reaction time was 2 hours.

The product was separated off from the reaction mixture by steam distillation at 130 mbar. The distillate was saturated with sodium chloride and extracted with methyl tert-butyl ether.

Boiling point: 61° C. (15 mbar).

The percentage catalyst figures specified in Table 1 correspond to the weights of the elements based on the total catalyst weight.

TABLE 1

| Catalyst | Reaction temperature | Yield |
| --- | --- | --- |
| 1.55 g of Pt on activated carbon (5% by weight) | 130° C. | 21% |
| 0.93 g of Pd on aluminum oxide (5% by weight) | 120° C. | 54% |

TABLE 1-continued

| Catalyst | Reaction temperature | Yield |
| --- | --- | --- |
| 1.24 g of Pd on aluminum oxide (5% by weight) | 120° C. | 53% |
| 2 g of activated nickel catalyst, molybdenum-doped | 120° C. | 30% |
| 2 g of activated nickel catalyst | 120° C. | 29% |
| 0.62 g of Raney nickel | 120° C. | 32% |
| 1.0 g of Pt/Rh on activated carbon (5% by weight) | 120° C. | 31% |

What is claimed is:

1. A process for producing 2-ethyl-3-methyl-1,4-diazine, characterized in that 2,3-pentanedione and 1,2-ethanediamine are reacted in, as solvent, an aliphatic monoalcohol, diol or triol containing three to eight carbon atoms with addition of catalytic amounts of an alkaline substance and are then added dropwise to a solution of an alkaline compound in an aliphatic monoalcohol, diol or triol having three to eight carbon atoms and a catalyst with dehydrogenating activity, which can be applied to a support, and the product is separated off by steam distillation.

2. The process as claimed in claim 1, characterized in that the solvent is butanol, pentanol, hexanol, heptanol, octanol, 1,2-butanediol, 1,4-butanediol, 1,3-propanediol, 1,2-propanediol or glycerol.

3. The process as claimed in claim 2, characterized in that the solvent is 1,3-propanediol, 1,2-propanediol or glycerol.

4. The process as claimed in claim 3, characterized in that the solvent is 1,2-propanediol.

5. The process as claimed in claim 1, characterized in that the amount of solvent in the first process step is between 10 and 300% by weight, based on 2,3-pentanedione.

6. The process as claimed in claim 1, characterized in that the alkaline substance is an alkali metal carbonate, an alkali metal hydrogencarbonate or alkali metal acetate.

7. The process as claimed in claim 6, characterized in that the alkaline substance is an alkali metal carbonate.

8. The process as claimed in claim 7, characterized in that the alkaline substance is potassium carbonate.

9. The process as claimed in claim 1, characterized in that the amount of alkaline substance is between 0.0001 to 40% by weight, based on 2,3-pentanedione.

10. The process as claimed in claim 1, characterized in that the first process step is carried out at −10 to 100° C.

11. The process as claimed in claim 1, characterized in that the second process step is carried out at 70 to 180° C.

12. The process as claimed in claim 1, characterized in that the catalyst with dehydrogenating activity contains the elements copper, silver, zinc, chromium, molybdenum, tungsten, manganese, rhenium, iron, ruthenium, osmium, cobalt, rhodium, iridium, nickel, palladium or platinum.

13. The process as claimed in claim 1, characterized in that the alkaline compound is an alkali metal alkoxide, alkali metal hydroxide or alkaline earth metal hydroxide.

* * * * *